United States Patent
Burhorst

(10) Patent No.: US 10,639,641 B2
(45) Date of Patent: May 5, 2020

(54) SOLIDS DISCHARGE MODULE

(71) Applicant: Hugo Vogelsand Maschinenbau GmbH, Essen (DE)

(72) Inventor: Torsten Burhorst, Garrel (DE)

(73) Assignee: Hugo Vogelsang Maschinenbau GmbH, Essen (DE)

( * ) Notice: Subject to any disclaimer, the term of this patent is extended or adjusted under 35 U.S.C. 154(b) by 367 days.

(21) Appl. No.: 15/538,439

(22) PCT Filed: Dec. 18, 2015

(86) PCT No.: PCT/EP2015/080630
§ 371 (c)(1),
(2) Date: Jun. 21, 2017

(87) PCT Pub. No.: WO2016/102394
PCT Pub. Date: Jun. 30, 2016

(65) Prior Publication Data
US 2017/0348697 A1    Dec. 7, 2017

(30) Foreign Application Priority Data
Dec. 22, 2014   (DE) .................... 20 2014 010 155 U

(51) Int. Cl.
*B02C 18/22* (2006.01)
*G01F 23/04* (2006.01)
(Continued)

(52) U.S. Cl.
CPC ...... *B02C 18/2225* (2013.01); *B02C 18/0092* (2013.01); *B02C 18/16* (2013.01);
(Continued)

(58) Field of Classification Search
CPC ... B07B 11/06; B07B 13/16; B02C 2018/164; B02C 13/286; B02C 13/28618;
(Continued)

(56) References Cited

U.S. PATENT DOCUMENTS 4,198,220 A   4/1980 Keller
5,074,435 A   12/1991 Suverkrop et al.
(Continued)

FOREIGN PATENT DOCUMENTS

CN    1868934 A    11/2006
CN    201447180 U    5/2010
(Continued)

OTHER PUBLICATIONS

China Patent Application No. 201580070471.2, Office Action dated Feb. 26, 2019.
(Continued)

*Primary Examiner* — Matthew Katcoff
(74) *Attorney, Agent, or Firm* — Kilpatrick Townsend & Stockton LLP; Dean W. Russell; Renae Bailey Wainwright

(57) ABSTRACT

The present invention concerns a solids discharge module (1) for discharging solids out of devices (100) carrying mixed fluid, in particular comminuting devices for solids contents in a mixed fluid, comprising a solids inlet (3), coupling means (31) for connecting the solids inlet (3) to a device (100) carrying a mixed fluid, a solids outlet (5), a closing member (9) which is arranged at the solids outlet (5) and is reciprocable between a release position and a blocking position, and a conveyor chamber (7) extending from the solids inlet (3) to the solids outlet (5). According to the invention it is proposed that a filling state detector (13) is provided which is adapted to detect and display a solids accumulation in the conveyor chamber (7).

15 Claims, 3 Drawing Sheets

Figure 1:
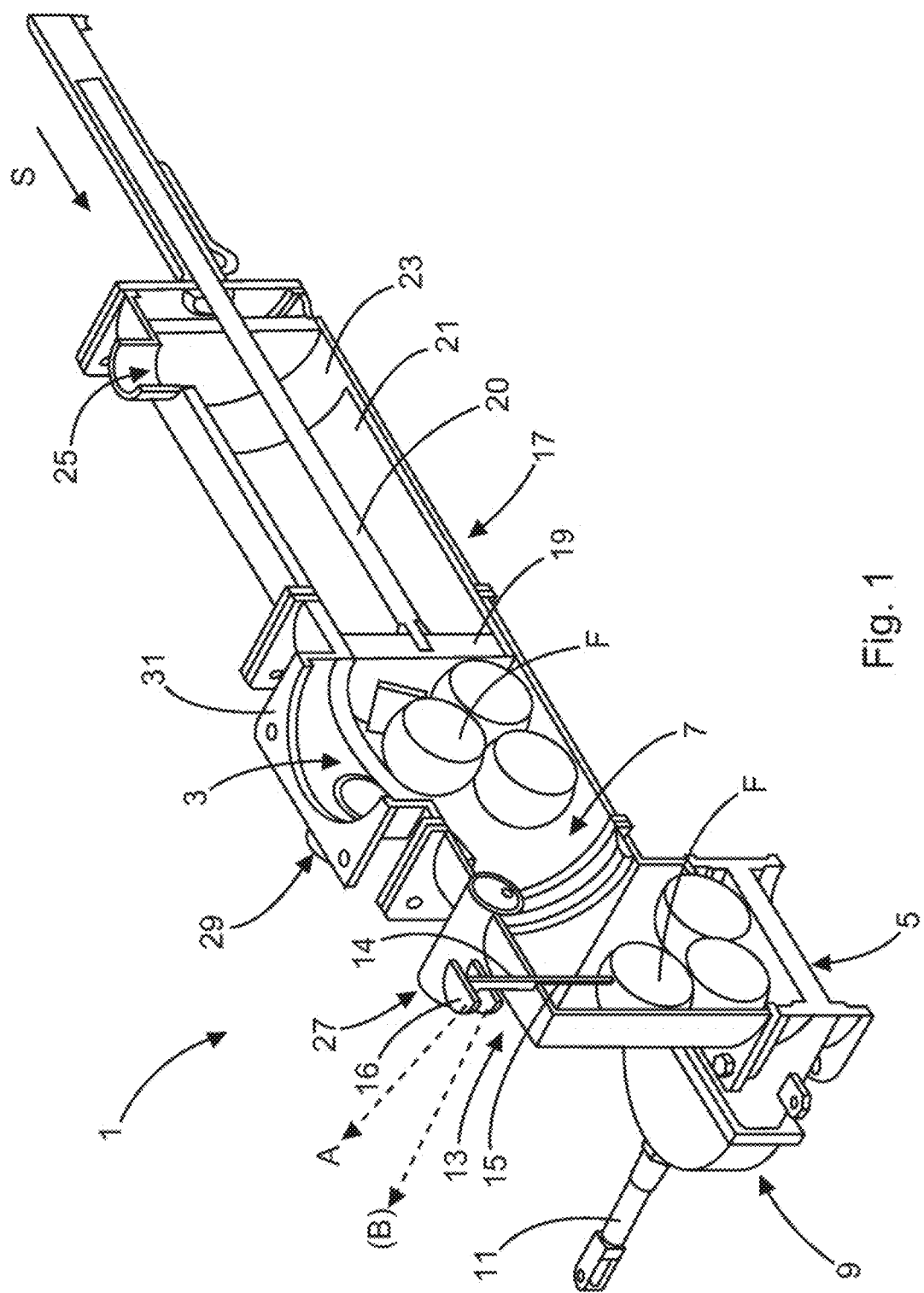

(51) Int. Cl.
*B02C 18/16* (2006.01)
*B02C 18/00* (2006.01)
*C12M 1/33* (2006.01)
*G05D 7/06* (2006.01)

(52) U.S. Cl.
CPC ............ *C12M 45/02* (2013.01); *G01F 23/04* (2013.01); *G05D 7/0605* (2013.01); *B02C 2018/164* (2013.01)

(58) Field of Classification Search
CPC ........ B02C 13/28609; B02C 13/28627; B02C 13/28672; B02C 18/22; B02C 18/2216; B02C 18/2233; B02C 17/1865; B02C 17/186; B02C 17/1835; B02C 23/36; B02C 23/182; B02C 18/0092; B02C 18/0084
See application file for complete search history.

(56) References Cited

U.S. PATENT DOCUMENTS

| | | | |
|---|---|---|---|
| 6,065,695 | A | 5/2000 | Shimasaki |
| 9,555,415 | B2 * | 1/2017 | Bouldin .................... B09B 3/00 |
| 2005/0067516 | A1 | 3/2005 | Irwin et al. |
| 2014/0306042 | A1 * | 10/2014 | Chesack ................. B02C 25/00 241/36 |

FOREIGN PATENT DOCUMENTS

| | | |
|---|---|---|
| CN | 202403286 U | 8/2012 |
| CN | 203184087 U | 9/2013 |
| CN | 203450636 U | 2/2014 |
| CN | 201058469 Y | 5/2018 |
| DE | 3026684 A1 | 2/1982 |
| DE | 202006003816 U1 | 7/2007 |
| GB | 2053727 A | 2/1981 |
| GB | 2308964 A | 7/1997 |
| JP | S53-124381 A | 10/1978 |
| JP | S5665796 U | 6/1981 |
| JP | S62144541 U | 9/1987 |
| JP | S62167091 U | 10/1987 |
| JP | S62-254858 | 11/1987 |
| JP | H07-000845 A | 1/1995 |
| JP | H7-136635 A | 5/1995 |
| JP | H08-001032 A | 1/1996 |
| JP | H8-187499 A | 7/1996 |
| JP | H9-268090 A | 10/1997 |
| JP | H9-271612 A | 10/1997 |
| JP | H10216690 | 8/1998 |
| JP | H11-108323 A | 4/1999 |
| JP | H11351741 A | 12/1999 |
| JP | 2001009306 | 1/2001 |
| JP | 2001-205015 A | 7/2001 |
| JP | 2003-093914 A | 4/2003 |
| JP | 2004-107061 A | 4/2004 |
| JP | 2005-324182 A | 11/2005 |
| JP | 2009045616 A | 3/2009 |
| JP | 2009-226466 A | 10/2009 |
| WO | H5-330602 A | 12/1993 |
| WO | 2004/087306 A1 | 10/2004 |

OTHER PUBLICATIONS

Korea Patent Application No. 10-2017-7020517, Office Action dated Apr. 16, 2019.
International Patent Application No. PCT/EP2015/080630, International Search Report (including English translation) and Written Opinion, dated Apr. 8, 2016, 14 pages.
Korean Patent Application No. 10-2017-7020517, Office Action (including English translation), dated Sep. 7, 2018.
Japan Patent Application No. 2017-533545, Office Action (including English translation), dated Jul. 3, 2018.
China Patent Application No. 201580070471.2, Office Action (including English translation), dated Jul. 2, 2018.
Japan Patent Application No. 2017-533545, Office Action dated Jun. 11, 2019.
International Patent Application No. PCT/EP2015/080630, Written Opinion of the International Searching Authority (including English translation), dated Apr. 8, 2016.
International Patent Application No. PCT/EP2015/080630, International Preliminary Report on Patentability, dated Jun. 27, 2017.
Office Action for Indian Patent Application No. 2017047025425 dated Oct. 10, 2019 (6 pages).
JP2017-533545, "Notice of Decision to Grant," dated Feb. 4, 2020, 3 pages.

* cited by examiner

SOLIDS DISCHARGE MODULE

CROSS REFERENCE TO RELATED APPLICATIONS

This patent application is the U.S. national stage entry of PCT/EP2015/080630 ("the '630 application"), filed on Dec. 18, 2015, which application is related to and claims priority benefits from German Application No. 20 2014 010 155.8 ("the '558 application"), filed on Dec. 22, 2014. The '630 and '558 applications are hereby incorporated in their entireties by this reference.

The present invention concerns a solids discharge module for discharging solids out of devices carrying mixed fluid, in particular comminuting devices for solids contents in a mixed fluid.

The invention concerns in particular such a discharge module as set forth in the classifying portion of claim 1. The invention further concerns a device as set forth in the classifying portion of claim 14 and a use of a solids discharge module on the afore-mentioned devices.

Mixed fluids confront the manufacturers of corresponding devices with the challenge that mixed fluids can be in themselves highly heterogeneous and of differing natures. Besides comparatively high-viscosity fluid components or fluids there may also be a solids loading content, for example in the form of stones, metal particles or the like.

Devices for conveying mixed fluid like for example rotary piston pumps, by virtue of their design principle, already enjoy a high level of tolerance for solids loading. Nonetheless in most cases the solids are unwanted constituents in the fluid flow. The solids contents either automatically settle in certain special regions of devices in order to be removed from the fluid flow or they are separated from the fluid flow in especially provided solids separators.

Apparatuses for processing mixed fluid, in particular comminuting devices like for example the RotaCut product series from Hugo Vogelsang Maschinenbau GmbH are integrated into the fluid flow in installations for mixed fluid conveyance or treatment in order to comminute solids contents entrained therein and prepare same for subsequent processing of the mixed fluid, for example in foodstuffs production or in biomass processing. It is also known from such installations that certain, particularly large and/or heavy, solids contents are separated out of the mixed fluid flow in collecting regions provided for that purpose, for example by means of sedimentation.

In the case of the above-described devices, in spite of the generally highly satisfactory mode of operation, there is nonetheless still the need for the solids contents which accumulate in the described manner to be removable reliably and with a low level of complication and expenditure. Accordingly the object of the invention is to provide a possible way of being able to remove those solids contents from the above-mentioned devices as efficiently as possible.

In a first aspect the invention attains that object with a solids discharge module as set forth in claim 1. The solids discharge module has a solids inlet, coupling means for connection of the inlet to a mixed fluid conveyor and/or processing device, a solids outlet, and a closing member which is arranged at the solids outlet and is reciprocable between a release position and a blocking position, and a conveyor chamber extending from the solids inlet to the solids outlet.

According to a first aspect the solids discharge module has a filling state detector adapted to detect and display a solids accumulation in the conveyor chamber. The filling state detector makes it easily possible, without having to interrupt operation of the respective device connected to the discharge module, to check whether a sufficient amount of solids has accumulated in the conveyor chamber, which justifies opening of the closing member for removal of the solids accumulation or would make that necessary.

According to a second aspect which alternatively or additionally attains the object of the invention the discharge module has a conveyor means which is arranged in the conveyor chamber and is adapted to convey solids fed to the solids inlet to the solids outlet. The conveyor means which according to the invention actively further conveys the solids fed thereto reduces a risk of blockage on the part of the connected conveyor and/or processing device.

The configurations hereinafter concern both the first and also the second aspects of the invention and are also to be found in the appendant claims.

In a preferred development of the invention the conveyor chamber extends inclinedly relative to the horizontal immediately upstream of the outlet, in particular vertically. That denotes the state in which the solids discharge module is in its operational orientation, that is to say for example a state connected to a device for conveying and/or processing mixed fluid.

By virtue of the inclined orientation of the conveyor chamber relative to the horizontal the accumulated solids automatically slip or drop out after the closing member is moved into the release position, which minimizes the risk of blockage of the discharge module at the outlet side.

In a preferred embodiment of the invention the closing member is in the form of a shut-off slide valve. Preferably the closing member is adapted to provide that its movement from the blocking position into the discharge position does not cause any displacement of the accumulated solids in opposite relationship to the discharge direction. That is achieved in a simple manner in the case of shut-off slide valves which do not have to perform any pivotal movement in or in opposite relationship to the flow direction or the discharge direction for release and blocking thereof.

In a further preferred embodiment the filling state detector is in the form of a probe having a probe body for introduction into the conveyor chamber. Manually or preferably also automatedly introducing the probe body into the conveyor chamber checks whether the probe body can penetrate into the conveyor chamber for example as far as its maximum depth of penetration or whether it encounters an obstacle before reaching the maximum depth of penetration. In connection with the present invention therefore a solids accumulation of sufficient amount is detected by virtue of the fact that the probe body cannot penetrate to its maximum depth of penetration, but already bears against the solids accumulation beforehand.

Particularly preferably the probe body has a display means which is visible from the exterior and is adapted to display whether the probe body can or cannot penetrate to its maximum penetration depth.

Further preferably the display means is adapted to display the actual depth of penetration of the probe body. While basically a qualitative indication as to whether the probe body can reach its maximum depth of penetration or already previously encounters an obstacle would be sufficient for reliable operation of the device and would be advantageous in regard to a possibly desired, particularly robust structure, it may also be desirable, for example by means of a scale, to be able to read off how far the probe body penetrates, or by what amount the probe body falls short of its maximum depth of penetration, in order to be able to assess the degree of accumulation of solids upstream of the outlet.

In a further preferred embodiment of the invention the conveyor means is in the form of a volume conveyor. Preferably the conveyor means has a piston slider which is moveable from the solids inlet in the direction of the solids outlet and is reciprocable between a retracted position and an extended position. A piston slider can be produced as a mechanically robust structure and can be actuated by means of a thrust rod which can be actuated externally manually or selectively by motor means. The form of the piston head and the peripheral side surfaces of the piston head can be precisely matched to a geometry of the conveyor chamber in order to ensure that they bear against the wall of the conveyor chamber, in a manner such as to ensure at any event that the solid contents to be discharged cannot pass, that is to say in sealing relationship against the wall. As the situation does not involve absolute material discharge but primarily the discharge of solid contents, a sufficiently small gap can remain between the piston slider and the conveyor chamber wall, through which for example liquid components which are also separated out can pass. The passing fluid is preferably circulated in the discharge module by means of suitable fluid inlet and outlets, or is discharged from the discharge module.

In an embodiment which is preferred because it is particularly robust the closing member is manually actuable. In a preferred alternative configuration which seeks to reduce the number of manually required interventions to the greatest possible extent the closing member is actuable by motor means. The term actuation by motor means is used in connection with the invention to denote electromagnetic, hydraulic or pneumatic actuation, wherein they are each respectively appropriately electrically controllable. Preferably the solids discharge module has an electronic control unit which is connected in signal-conducting relationship both to the filling state detector and also to the corresponding drive of the closing member. Further preferably the electronic control unit is adapted to actuate the drive of the closing member for the movement thereof from the blocking position into the release position, for example by means of suitable voltage signals, when the filling state detector outputs a representative signal by means of the signal-conducting connection, to the effect that there is an adequate solids accumulation at the solids outlet. For example the filling state detector could have a simple voltage switch which distinguishes between two switching states; a first switching state in which the filling state detector signals no switching need for the closing member, and a second switching state in which the filling state detector signals a switching need for the closing member. If the filling state detector is in the form of a probe body the attainment of the maximum depth of penetration or another predetermined depth of penetration could represent the first switching state, and a failure to reach the maximum depth of penetration or the other predetermined depth of penetration could represent the second switching state.

In a further aspect the invention also attains its object by a solids discharge module for the discharge of solids out of devices carrying mixed fluid, in particular comminuting devices for solids contents in a mixed fluid, comprising a solids inlet, coupling means for connection to a device carrying a mixed fluid, a solids outlet, and a collecting chamber extending from the solids inlet to the solids outlet, and a filling state detector adapted to detect and display a solids accumulation in the collecting chamber. The filling state detector is preferably designed in accordance with the above-described preferred embodiments and implements the same advantages, for which reason attention is directed in this respect to the foregoing description. It is preferred in this aspect for the collecting chamber to be inclined relative to the horizontal (in relation to the operationally ready orientation of the discharge module) in such a way that the solids passing into the collecting chamber through the solids inlet automatically slip or drop in the direction of the solids outlet, assisted by the force of gravity. Particularly preferably the collecting chamber is in the form of a vertical collecting tube or a vertical collecting hopper.

In a mixed fluid-carrying device as described in the opening part of this specification the invention attains its object in that the device has a collecting region for solids separated from the mixed fluid, and an outlet communicating with the collecting region, wherein a solids discharge module is connected to the outlet, that is in accordance with one of the preferred embodiments described herein.

Preferably provided in those devices are coupling means for connection of the solids discharge module, that co-operate with the coupling means of the solids discharge module. Preferably reversibly releasable coupling means are used, preferably for force-lockingly or positively lockingly connecting the discharge module to the device. Among the devices for processing mixed fluid it is particularly preferred that the discharge module according to the invention is to be connected to a comminuting device for solids contents in mixed fluids.

The above-mentioned devices involve the same preferred configurations and involve the same advantages as have already been discussed in relation to the solids discharge module according to the invention. In that respect attention is directed to the foregoing description.

The invention further concerns a use of a solids discharge module. The invention attains its object insofar as a solids discharge module in accordance with one of the preferred embodiments described herein is used on a device for conveying and/or processing mixed fluid, in particular a comminuting device for solids contents in mixed fluids for removing separated solids.

Figure 2:
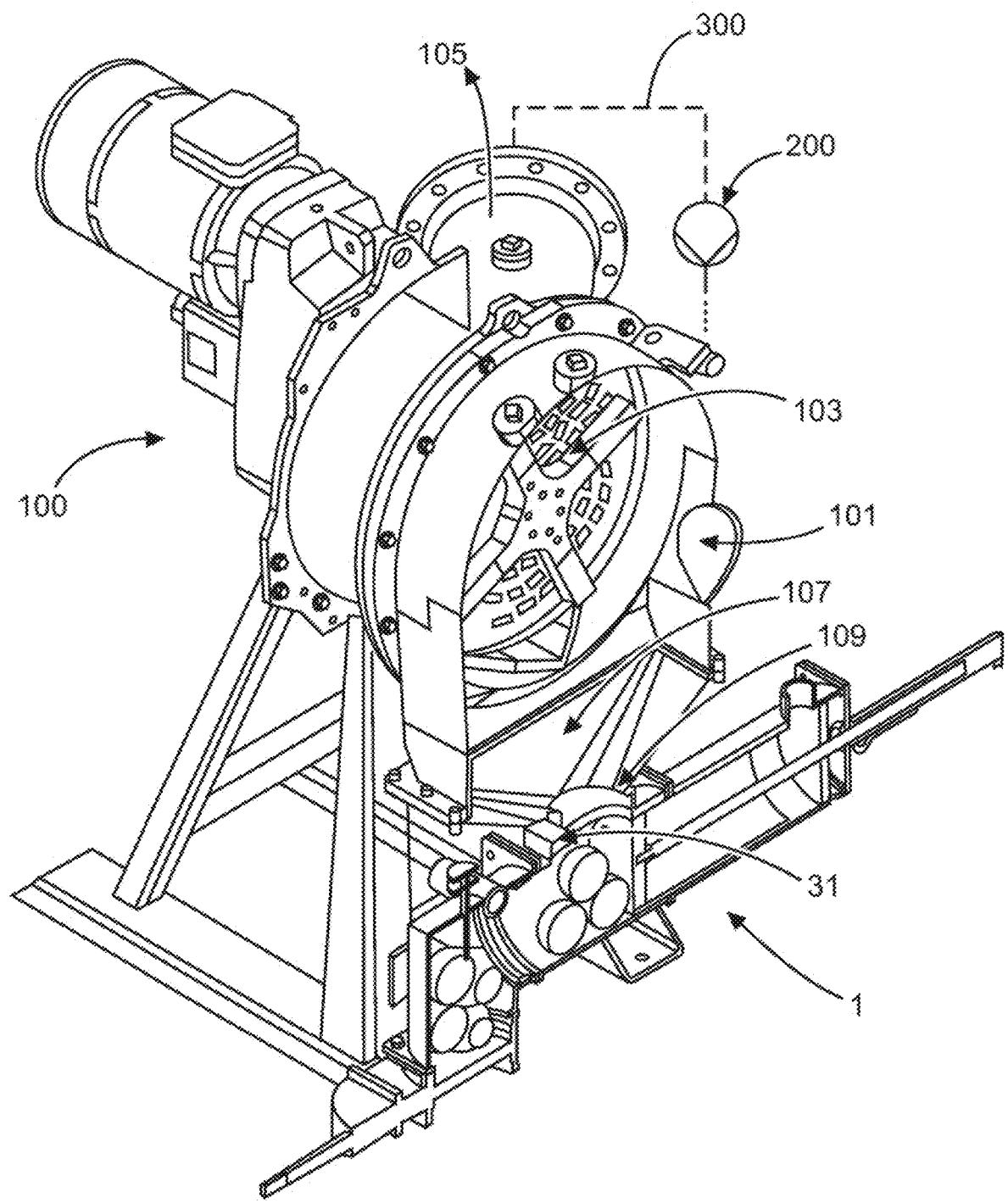
Figure 3:
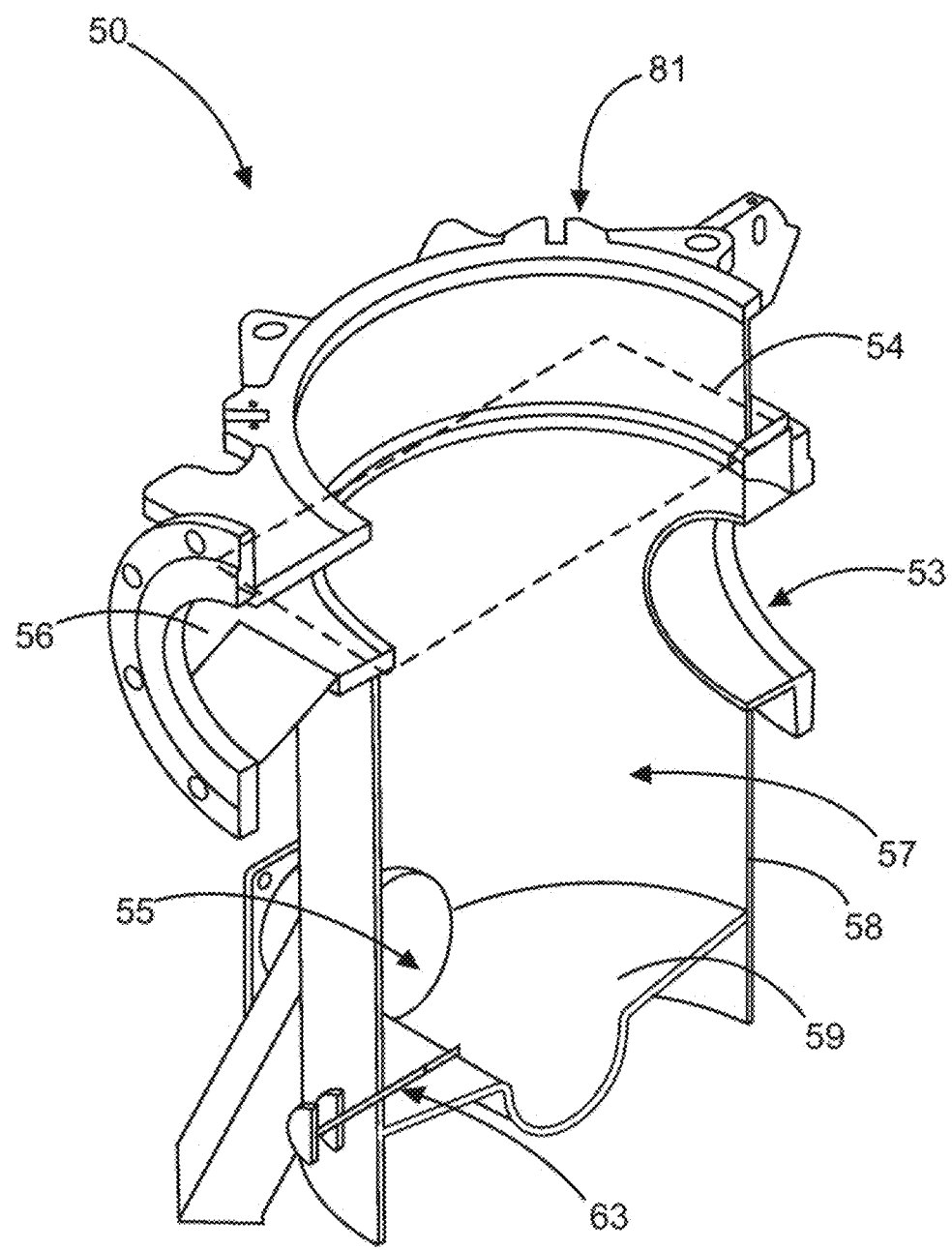

The invention is described in greater detail hereinafter by means of preferred embodiments with reference to the accompanying Figures in which:

FIG. 1 is a diagrammatic perspective sectional view of a solids discharge module according to a first preferred embodiment, FIG. 2 is a diagrammatic perspective view in partial section of a device for processing and/or conveying mixed fluids having a discharge module as shown in FIG. 1, and FIG. 3 is a diagrammatic perspective sectional view of a solids discharge module in accordance with a second preferred embodiment.

FIG. 1 shows a solids discharge module 1 according to a preferred embodiment of the invention. The solids discharge module 1 has a solids inlet 3 and a solids outlet 5. A conveyor chamber 7 extends between the solids inlet 3 and the solids outlet 5. Downstream of the inlet 3 the conveyor chamber 7 initially involves an orientation which is horizontal in the connected state of the discharge module. In an end portion upstream of the solids outlet 5 the conveyor chamber 7 is inclined relative to the horizontal, more specifically being oriented vertically.

A closing member 9 is arranged out of the solids outlet 5. The closing member 9 in the present case is in the form of a shut-off slide valve and is moveable by means of an actuating element 11 from the illustrated blocking position into a release position, and back again.

A filling state detector 13 for solids contents F is arranged in the conveyor chamber 7. The filling state detector 13 has a probe body 15, on which a sensing head 16 is arranged outside the conveyor chamber on a housing portion of the discharge module 1. In FIG. 1 the sensing head 16 is in a fixed position A of being pushed out. The probe body 15 can be moved into the interior of the conveyor chamber 7 against the return force of a spring 14, more specifically until either it reaches its maximum depth of penetration, or however until it encounters solids F which have accumulated upstream of the solids outlet 5, for example in the position indicated by the arrow B.

A piston slider 17 is arranged in the region of the solids inlet 3 at the right in FIG. 1 beside the cross-section of the solids inlet 3. The piston slider 17 has a piston head 19 which is moveable by means of a thrust rod 20 through the conveyor chamber 7 in the direction of the solids outlet 5. A piston casing 21 extends from the piston head 19 in opposite relationship to a direction S in which the piston head 19, starting from the position in FIG. 1 (retracted position) would be moved in the direction of an extension position. The piston casing 21 closes the solids inlet 3 when the piston slider 17 is moved in the direction S through the conveyor chamber.

The piston casing 21 faces towards the wall 23 of the conveyor chamber and either bears against it or forms a gap with the wall 23 of the conveyor chamber 7, the gap preferably being so small that solids cannot pass through it. In this respect, the term solids is used to denote those particles or items which, in an upstream-connected device 100 (see FIG. 2) carrying mixed fluid and connected by way of coupling means 31 at the inlet side to the discharge module 1, have been separated off because they are too large and too heavy to remain in the fluid flow there.

There is also a connection 25 to which optionally it is possible to connect a line connecting the space between the piston casing 21 and the wall 23 to the pipe downstream of a cutting mechanism 103 of the device 100. That has the advantage that sealing integrity does not have to be provided between the piston head 19 and the conveyor chamber 7.

The process involved in discharge also involves fluid being pushed in the direction of the solids outlet 5. That fluid can be returned to the device 100 by way of the connection 27. A displacement process takes place due to the pushing movement. So that the pressure does not rise the fluid is preferably recycled.

Fluid can be injected again by way of a connection 29. The injection of water at that location is intended to promote improved separation of solid bodies.

The solids discharge module 1 shown in FIG. 1 is illustrated in FIG. 2 in its use on a mixed fluid-carrying device 100. The device 100 has a mixed fluid inlet 101, a rotational cutting mechanism 103 and a mixed fluid outlet 105 arranged beyond the rotational cutting mechanism 103. The mixed fluid-carrying device 100 is accordingly in the form of a comminuting device, as are known for example from the "RotaCut" product series from Hugo Vogelsang Maschinenbau GmbH. As a comminuting device like for example the type shown in FIG. 1 does not provide its own conveyor action a fluid conduit system 300 is preferably connected downstream of the mixed fluid-carrying device 100, with a pump 200, for example a rotary piston pump, additionally being arranged in the fluid conduit system 300.

The device 100 has a collecting region 107 in which those solids are separated off, which are too large and/or too heavy for them—entrained by the fluid flow—to be comminuted by the rotational cutting mechanism 103 and to leave the device 100 again through the fluid outlet 105.

At an outlet 109 arranged at the lower end of the collecting region 107 the solids discharge module 1 is connected with its solids inlet by means of suitable coupling means 31.

In the present embodiment a comminuting device is shown as the mixed fluid-carrying device 100 by way of example. Instead of a comminuting device however in accordance with the invention other mixed fluid-carrying devices are also provided, having a container in which solids settle, like for example heavy matter separators, solids metering means, for example from Hugo Vogelsang Maschinenbau GmbH, known by the name QuickMix, two-shaft mashers, for example from Hugo Vogelsang Maschinenbau GmbH, known by the name XRipper, tanker trucks or pump connections.

FIG. 3 shows a discharge module according to a second embodiment of the invention. Instead of an expulsion mechanism and a conveyor chamber the solids discharge module 50 shown in FIG. 3 has a collecting chamber 57 which is preferably arranged vertically in operation. A mixed fluid and solids inlet 53 is arranged in the collecting chamber 57, at top right in FIG. 3. Disposed above the solids inlet 53 is a flange plane 54, at whose height approximately the cutting mechanism 103 of the device 100 can be disposed in the assembled position. A fluid outlet 56 is provided downstream of the plane 54 for the comminuting device 103, above the plane 54, at the left in FIG. 3. At its top side the discharge module 50 has coupling means 81 for connection to a mixed fluid-carrying device like for example the device 100 in FIG. 2.

The collecting chamber 57 is provided in the interior of a cylindrical tube 58, at the lower end of which is disposed a solids outlet 55, also referred to as the cleaning orifice. The solids outlet 55 is optionally closeable with a closing member, for example in the form of a shut-off slide valve, as in the first embodiment.

A filling state detector 63 is arranged in the proximity of the bottom 59 of the collecting chamber 57. As in the first embodiment the filling state detector 63 is also adapted to detect the presence of solids at the lower end of the collecting chamber. The height at which the filling state detector is mounted determines the moment in time at which a need for emptying is displayed.

The invention claimed is:

1. A solids discharge module for discharging solids out of devices carrying mixed fluid comprising:
   a solids inlet couplable with a device carrying a mixed fluid;
   a solids outlet;
   a closing member which is arranged at the solids outlet and is reciprocable between a release position and a blocking position;
   a conveyor chamber extending from the solids inlet to the solids outlet;
   a filling state detector adapted to detect and display a solids accumulation in the conveyor chamber;
   a motor coupled to the closing member; and
   an electronic control unit connected in signal communication with the filling state detector and the motor,
   wherein:
   the closing member is actuable by the motor; and
   the electronic control unit is configured to actuate the motor to move the closing member from the blocking position into the release position when the filling state detector outputs a representative signal that there is a sufficient solids accumulation at the solids outlet.

2. A solids discharge module as set forth in claim 1, further comprising a conveyor means which is arranged in the conveyor chamber and is adapted to convey solids fed to the solids inlet to the solids outlet.

3. A solids discharge module as set forth in claim 1, wherein at least a portion of the conveyor chamber extends vertically relative to horizontal immediately upstream of the outlet.

4. A solids discharge module as set forth in claim 1, wherein the closing member is in the form of a shut-off slide valve.

5. A solids discharge module as set forth in claim 1, wherein the filling state detector is in the form of a probe having a probe body for introduction into the conveyor chamber.

6. A solids discharge module as set forth in claim 5, wherein the probe body has a display means which is visible from the exterior and is adapted to display whether the probe body can or cannot penetrate to its maximum penetration depth.

7. A solids discharge module as set forth in claim 6, wherein the display means is adapted to display the actual depth of penetration of the probe body.

8. A solids discharge module as set forth in claim 2, wherein the conveyor means is in the form of a volume conveyor.

9. A solids discharge module as set forth in claim 8, wherein the conveyor means has a piston slider which is moveable from the solids inlet in the direction of the solids outlet and is reciprocable between a retracted position and an extended position.

10. A solids discharge module as set forth in claim 9, wherein the piston slider has a piston head and a piston casing extending peripherally from the piston head away from the conveyor chamber, wherein the piston casing is adapted to close the solids inlet when the piston slider is moved from the retracted position into the extended position.

11. A device carrying a mixed fluid comprising:
a collecting region for solids separated from the mixed fluid,
an outlet communicating with the collecting region, and
a solids discharge module as set forth in claim 1, wherein the solids discharge module is connected to the outlet.

12. A device as set forth in claim 11, wherein the device is couplable with the solids discharge module via force-locking, positively locking or reversibly releasable coupling.

13. A device as set forth in claim 11, wherein the device is a comminuting device for solids contents in mixed fluids.

14. A method for removing separated solids from a device carrying mixed fluid comprising:
providing the device carrying the mixed fluid, the device comprising a collecting region for solids separated from the mixed fluid, a device outlet communicating with the collecting region, and a solids discharge module connected to the device outlet, wherein the solids discharge module comprises:
a solids inlet couplable with the device carrying the mixed fluid;
a solids outlet;
a closing member arranged at the solids outlet and is reciprocable between a release position and a blocking position;
a conveyor chamber extending from the solids inlet to the solids outlet;
a filling state detector adapted to detect and display a solids accumulation in the conveyor chamber;
a motor coupled to the closing member and configured to activate the motor; and
an electronic control unit connected in signal communication with the filling state detector and the motor, and
when the filling state detector outputs a representative signal that there is a sufficient solids accumulation at the solids outlet, activating the motor via the electronic control unit to move the closing member from the blocking position into the release position and discharge the solids accumulation from the solids outlet into the collecting region.

15. A solids discharge module as set forth in claim 1, wherein at least a portion of the conveyor chamber extends inclinedly relative to horizontal immediately upstream of the outlet.

* * * * *

UNITED STATES PATENT AND TRADEMARK OFFICE
CERTIFICATE OF CORRECTION

PATENT NO. : 10,639,641 B2  
APPLICATION NO. : 15/538439  
DATED : May 5, 2020  
INVENTOR(S) : Torsten Burhorst Page 1 of 1

It is certified that error appears in the above-identified patent and that said Letters Patent is hereby corrected as shown below:

On the Title Page

In item (71), in Column 1, in "Applicant", Line 1, delete "Vogelsand" and insert -- Vogelsang --, therefor.

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*